(12) United States Patent
Plechinger

(10) Patent No.: US 9,184,008 B2
(45) Date of Patent: Nov. 10, 2015

(54) RELAY FOR A DEFIBRILLATOR

(71) Applicant: Gerhard Plechinger, Villingen-Schwenningen (DE)

(72) Inventor: Gerhard Plechinger, Villingen-Schwenningen (DE)

(73) Assignee: Metrax GmbH, Rottweil (DE)

( * ) Notice: Subject to any disclaimer, the term of this patent is extended or adjusted under 35 U.S.C. 154(b) by 0 days.

(21) Appl. No.: 14/373,000

(22) PCT Filed: Nov. 26, 2012

(86) PCT No.: PCT/EP2012/073571
§ 371 (c)(1),
(2) Date: Jul. 17, 2014

(87) PCT Pub. No.: WO2013/107546
PCT Pub. Date: Jul. 25, 2013

(65) Prior Publication Data
US 2015/0137917 A1 May 21, 2015

(30) Foreign Application Priority Data

Jan. 17, 2012 (DE) ..................... 20 2012 100 155 U

(51) Int. Cl.

| | |
|---|---|
| *H01H 50/64* | (2006.01) |
| *A61N 1/39* | (2006.01) |
| *H01H 50/24* | (2006.01) |
| *H01H 50/58* | (2006.01) |
| *H01H 50/60* | (2006.01) |
| *H01H 50/30* | (2006.01) |

(52) U.S. Cl.
CPC ............... *H01H 50/643* (2013.01); *A61N 1/39* (2013.01); *A61N 1/3912* (2013.01); *A61N 1/3968* (2013.01); *H01H 50/24* (2013.01); *H01H 50/30* (2013.01); *H01H 50/58* (2013.01); *H01H 50/60* (2013.01)

(58) Field of Classification Search
CPC ..... H01H 1/26; H01H 50/641; H01H 50/643; H01H 50/24
See application file for complete search history.

(56) References Cited

U.S. PATENT DOCUMENTS

| 2,638,514 | A | * | 5/1953 | Martin ......................... 200/1 A |
| 3,800,250 | A | * | 3/1974 | Mori et al. .................... 335/128 |
| 3,814,105 | A | | 6/1974 | Howard et al. |
| 4,216,452 | A | | 8/1980 | Arnoux et al. |
| 4,825,179 | A | * | 4/1989 | Nagamoto et al. .............. 335/80 |
| 5,072,328 | A | * | 12/1991 | Dvorak et al. ................ 361/210 |
| 5,852,392 | A | | 12/1998 | Aharonian |
| 6,184,484 | B1 | * | 2/2001 | Wade, III ...................... 200/284 |
| 2006/0036287 | A1 | | 2/2006 | Bucher |
| 2010/0013580 | A1 | * | 1/2010 | Parker et al. .................. 335/167 |

FOREIGN PATENT DOCUMENTS

| DE | 28 27 650 C2 | 4/1982 |
| DE | 102 54 482 B4 | 6/2008 |

* cited by examiner

*Primary Examiner* — Mohamad Musleh
(74) *Attorney, Agent, or Firm* — Pauley Erickson & Kottis

(57) ABSTRACT

A relay for a defibrillator, including a support base on which a coil and a contacting unit having a contact assembly are mounted. The contacting unit can be actuated by an armature and at least one additional mechanical connecting link as a result of the electrical excitation of the coil. The contact assembly has contacts supported on contact carriers. The contacts can be connected to each other by activating the coil. In order to optimize the contacting, at least one connecting link can be designed as a rotating lever coupled to the armature, which rotating lever is pivotably coupled to a contact carrier, and another contact carrier is pivotably coupled to an additional rotating lever or directly to the armature, wherein both contact carriers having the contacts to be contacted are moved towards each other during contacting.

14 Claims, 3 Drawing Sheets

RELAY FOR A DEFIBRILLATOR

BACKGROUND OF THE INVENTION

1. Field of the Invention

This invention relates to a relay for a defibrillator, having a support base on which are mounted a coil and a contacting unit with a contacting mechanism. The contacting unit, through excitation of the coil, can be actuated via an armature and at least one other mechanical intermediate element and has contacts that are supported on contact supports, which are separate, such as are not electrically connected to each other in the open state, and can be brought into contact with or moved away from each other through activation of the coil.

2. Discussion of Related Art

A relay of this kind is used, among other things, in defibrillators in order to deliver an electrical pulse from a high-voltage unit via electrodes to the body of a patient, as described in German Patent Reference DE 102 54 482 B4. For successful defibrillation, an exact synchronization of the impulse to detected signals of coronary activity is of critical importance. Delays on the order of magnitude of 10 to 15 ms, for example, which occur as the contacts are traveling through the movement paths and which are also due to the bouncing of the contacts, can have a very negative impact on the defibrillation effect. For example, an increased defibrillation energy can be required if the optimum timing is not achieved. In addition, relays often have significant quality differences and variations in the switching precision due to manufacturing tolerances.

Another electromagnetic relay is disclosed in German Patent Reference DE 28 27 650 C2. This relay has a first and second fixed contact that are stationary relative to the electromagnet and that are mounted on a contact support that is affixed in an insulating socket. In addition, a third fixed contact can be provided, which is affixed in the socket in a corresponding fashion. Furthermore, two U-shaped contact supports are provided, which have a first and second leg and, respectively, a third and fourth leg, with ends having contacts that can be brought into electrically conductive contact with the fixed contacts by a control mechanism or with a different switching, can be moved apart from each other in order to break the electrical connection. With two movable control mechanisms, the two legs of the same U-shaped, spring-elastic contact support with the contacts situated at their ends can be moved toward each other to achieve a disconnection from the associated fixed contacts or, with a movement of the two control mechanisms in the opposite direction due to their spring-elasticity, are moved apart from each other in order to produce a contact with the associated fixed contacts. Here, also, the movement paths of the contacts situated on the same contact support are relatively large, which can result in significant disadvantages in contact making.

SUMMARY OF THE INVENTION

One object of this invention is to provide a relay for a defibrillator of the type mentioned above, but which is optimized with regard to a precise contact making and a defibrillator equipped therewith.

This object is attained by the features of this invention as taught in this specification and the claims.

In one embodiment of this invention, a relay with features according to this invention has at least one intermediate element embodied as a pivot lever coupled to the armature and pivotably coupled to the one of the contact supports, which supports one of the contacts to be brought into contact with each other, and another contact support, which supports the other of the contacts to be brought into contact with each other, is coupled to another pivot lever or is pivotably coupled directly to the armature, and during the contacting procedure, the two contact supports with the contacts, to be brought into contact with each other, are moved toward each other in a guided fashion.

In a relay with features according to one embodiment of this invention, the intermediate elements have a pivot lever mechanism, which is coupled to the armature and has at least two pivot levers, one of which is pivotably connected to the contact support of the contact pair and at least one of which is pivotably coupled to a separate lateral contact support. The pivot levers are supported on the support base in pivoting fashion so that both the contact support of the contact pair and the contact support with the lateral contact, which is to be contacted, are moved toward each other in a guided fashion during the contacting procedure.

These measures significantly shorten, preferably by half, the movement path that the contacts must travel during the contacting procedure. This also makes it possible to reduce bounce phenomena so that on the whole, the contacting time until the precise contact is significantly shortened. According to some embodiments of this invention, this can also be used for relays with simple closing and opening functions, or can be used for relays with changeover procedures that are improved.

A defibrillator having at least one relay embodied in this way yields an increased precision in contact, particularly over the longer term.

In another embodiment, at least one contact support is embodied in the form of a contact support that is spring-elastic in the pivoting direction. The guided contact, however, can also be used with pivotably supported, rigid contact supports or with a combination of pivotably supported, rigid contact supports and spring-elastic contact supports.

In another embodiment, the design and function includes the pivot lever or levers supported in a pivoting fashion on a respective fixed support element, mounted on a bearing plate of the support base.

In another embodiment, from a production standpoint, the pivot levers are produced in the form of shaped parts, in particular parts stamped out of a flat material.

In other embodiments, for the production and function, with simple, advantageous possibilities adapted to different relay types, are produced if the pivot levers are coupled to each other in a pivotable, pivoting-motion-transmitting fashion by coupling sections in the form of rounded cut-outs and complementary coupling counterpart sections.

In another embodiment, the design and function provides between their bearing point on the respective bearing element and the respective contact, the pivot levers having at least one pivot lever support piece on which the contact supports of the relevant contacts are supported for the pivoting action. For example, when a pivot lever is of flat material, the pivot lever support pieces can be embodied as bent sections that protrude at right angles from the plane of the pivot lever or can be embodied as stud-like protrusions attached thereto.

BRIEF DESCRIPTION OF THE DRAWINGS

This invention is explained in greater detail in view of exemplary embodiments with reference to the drawings, wherein.

DETAILED DESCRIPTION OF THE INVENTION

Figure 1:
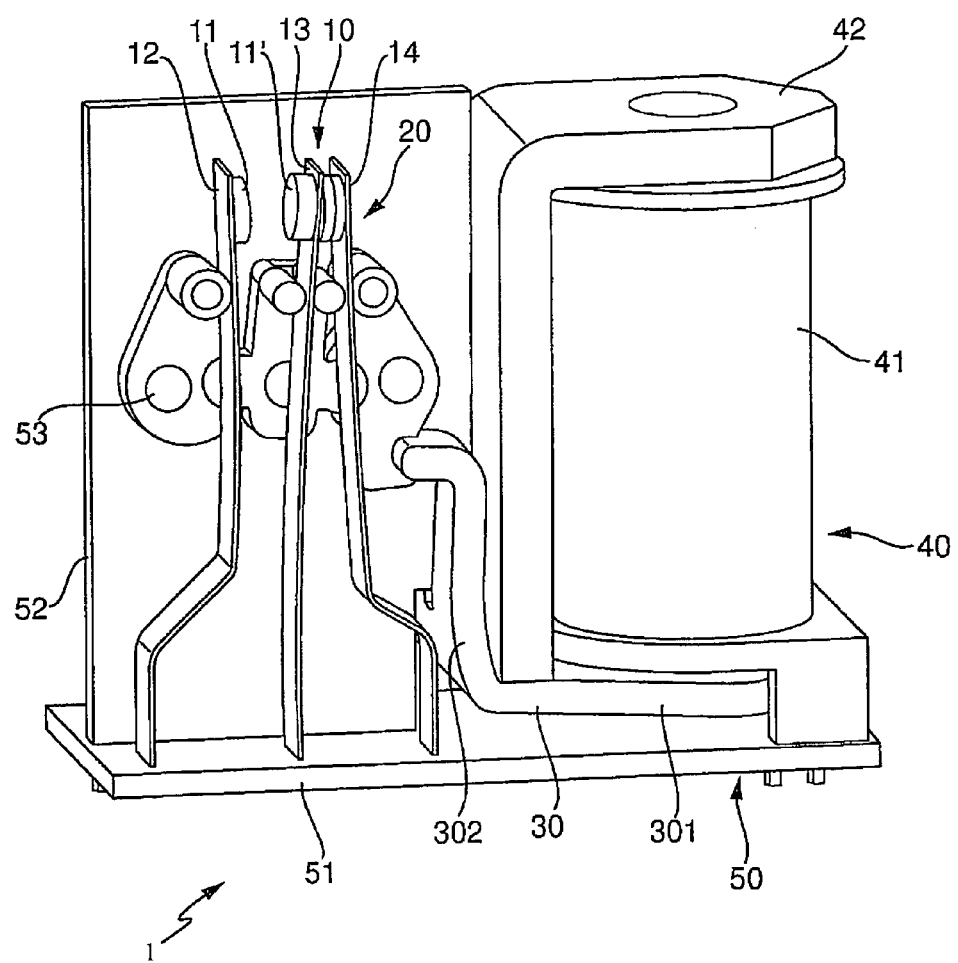
FIG. 1 is a perspective view of a relay with a changeover mechanism, according to one embodiment of this invention.

FIG. 1 shows a perspective side view of a relay 1 with a support base 50 on which are mounted a coil 40 and a contacting unit 10, which can be actuated by the coil 40 via an armature 30 and other mechanical intermediate elements in the form of a pivot lever mechanism 20.

Figure 2A:
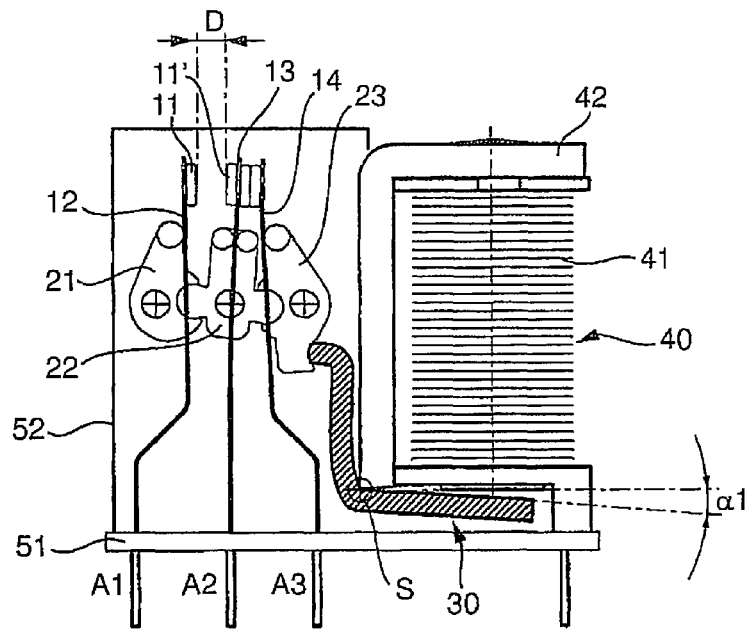
FIGS. 2A and 2B show side views of a relay according to FIG. 1, in two different contact positions.
Figure 2B:
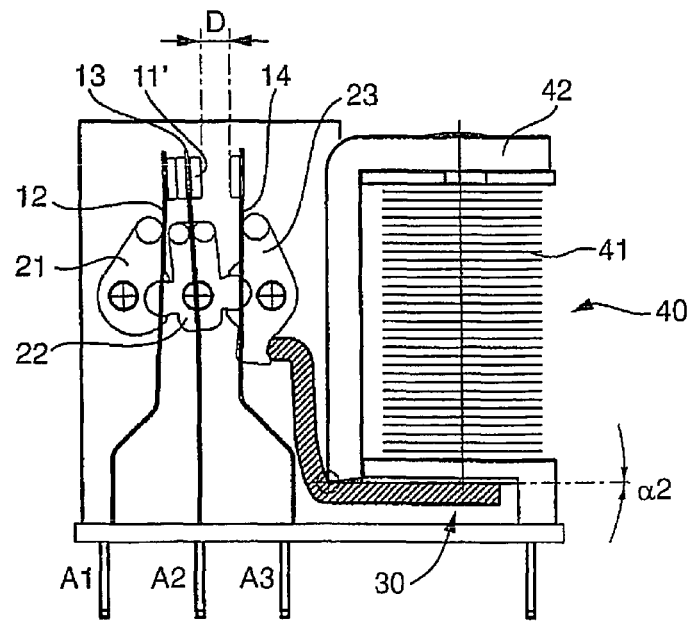
Figure 3A:
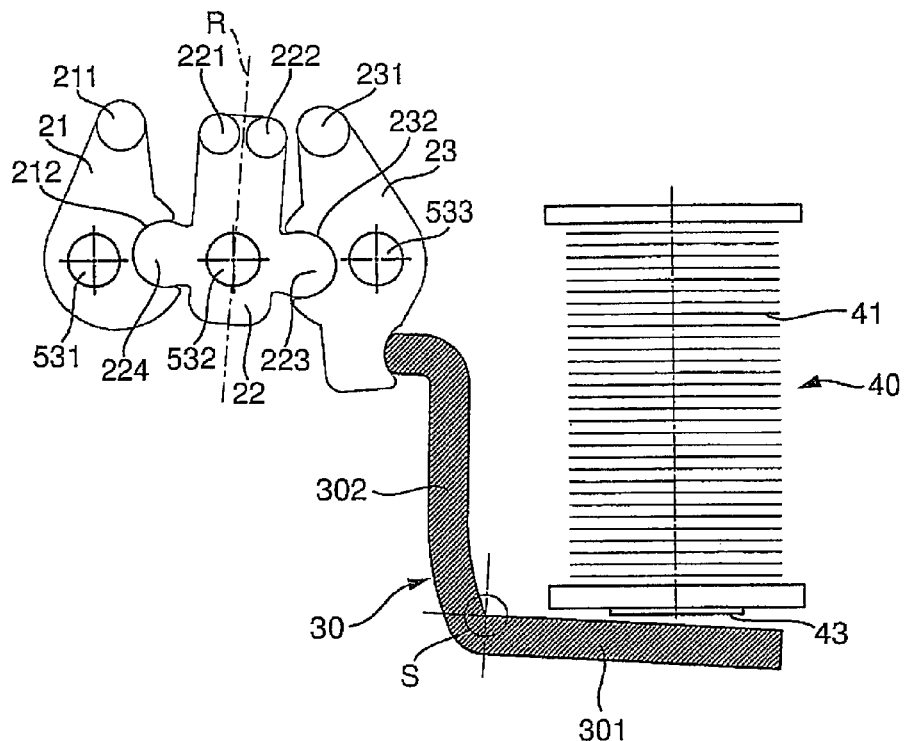
FIGS. 3A and 3B show side views of the moving parts of the relay according to FIG. 1, in the two different contact positions shown in FIGS. 2A and 2B.
Figure 3B:
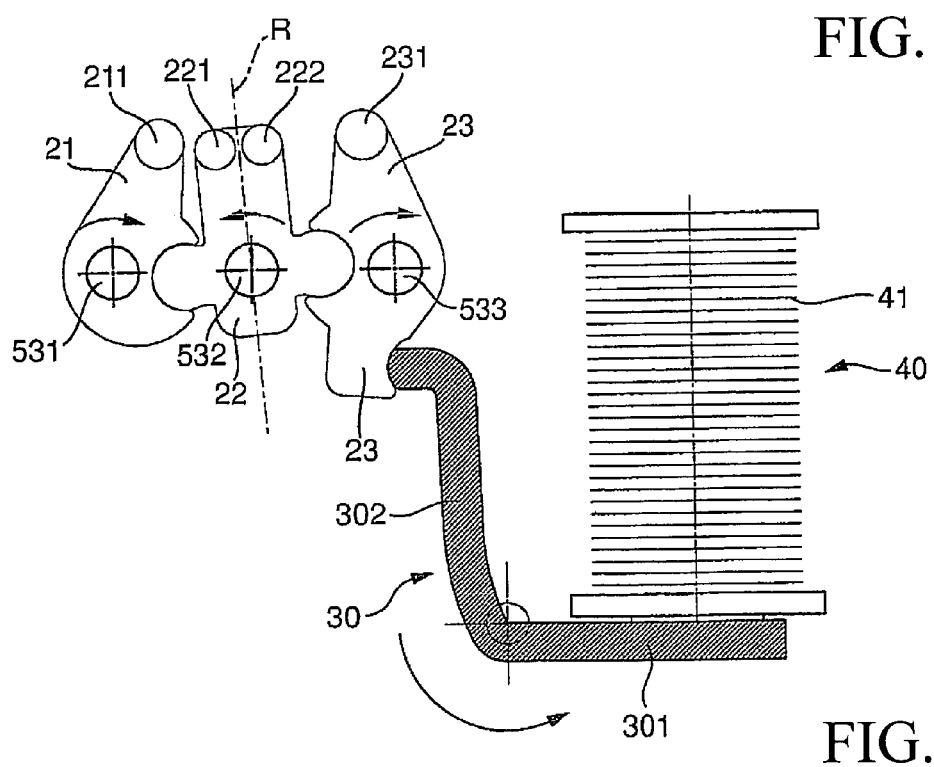

The coil 40 is secured to a coil support 42 and has a winding 41, which surrounds a core 43 (see FIG. 3A). The coil 40 is excited when supplied with electricity and acts in an intrinsically known way on the armature 30, which is pivotably supported on a lower end section of the coil support 42 at a fulcrum S (see FIG. 2A) and by electromagnetic force, is attracted at its release lever 301, thus causing a control lever, which is oriented upward in FIG. 1, to pivot toward the left. When the coil 40 is not excited, the control lever 302 advantageously pivots back, such as toward the right in FIG. 1, by a spring force. These events are also shown in FIGS. 2A, 2B, 3A, and 3B, which show the pivoting of the armature 30 around the fulcrum S by a pivoting angle α1 with a change in the direction R of the pivoting position. FIGS. 2B and 3B show the attracted state of the armature 30, yielding an angular position α2 of 0°.

The contacting unit 10 can be embodied in the form of a changeover contact mechanism, with two lateral contact supports, namely a first contact support 12 and a third contact support 14, and a middle contact support that is separate from these, such as a second contact support 13, as shown in FIGS. 1, 2A, and 2B. The contact supports 12, 13, 14 in the form of contact fingers are attached by their respective lower end section to abase plate 51 of the support base 50 and in their respective upper end region, on the sides oriented toward one another, and have contacts 11, 11'. The middle contact support 13 has contacts 11' on both sides, forming a contact pair. The contact supports 12, 13, 14 are pivotable so that in alternating fashion, the armature 30 can bring their contacts 11, 11' into contact, in the sense of directly resting against each other or touching with each other or with different switching separate them from each other in order to make or break an electrically conductive connection. Between the respectively opened contacts, there is then a distance D. In order to make the contact, the surfaces that are to contact each other must move across the distance D along a movement path, as is evident by comparing FIGS. 2A and 2B. From the non-attracted pivot position at the pivot angle α1, into which the armature 30 is brought by the spring force of at least one spring-elastically embodied contact support 12, 13, 14 and in which the two contacts 11, 11' on the right are contacted (see FIG. 2A), the armature 30 in this case is brought into the angular position α2 into which it is attracted by the coil 40, in which the two contacts 11, 11' on the left contact each other (see FIG. 2B). In this case, the armature 30 acts on the contact supports 12, 13, 14 via the pivot lever mechanism 20.

The pivot lever mechanism 20 has three pivot levers, namely a first pivot lever 21, which is coupled to the first contact support 12 via a pivot lever support piece 211, a second pivot lever 22, which is coupled to the second contact support 13 via a first and second pivot lever support piece 221, 222, and a third pivot lever 23, which is coupled to the to the third contact support via a pivot lever support piece 231, as is shown in greater detail in FIGS. 3A and 3B. The pivot levers are supported in a pivotable fashion on bearing elements 53 on a bearing plate 52 mounted on the base plate 51 at right angles thereto and parallel to the pivoting plane, namely the first pivot lever 21 on a first pivot bearing 531, the second pivot lever 22 on a second pivot bearing 532, and the third pivot lever 23 on a third pivot bearing 533, as is also shown in FIGS. 2A, 2B, 3A, and 3B. The third pivot lever 23 situated closest to the coil 40 in this case is coupled with its lower pivoting section to the control lever 302 of the armature 30, while the second pivot lever 22 situated in the middle is pivotably coupled with its lever arm, which is situated on the right relative to the pivot bearing 532, to the opposing left lever arm of the third pivot lever 23 and is pivotably coupled with its lever arm on the left to the opposing right lever arm of the first pivot lever 21. The pivot lever support pieces are each arranged on a respective upper lever arm of the pivot levers 21, 22, 23 thus engaging with the associated contact supports 12, 13, 14 in their upper region between the first, second, and third pivot bearing 531, 532, 533, respectively, in order to move the latter.

As the schematic depictions in FIGS. 3A and 3B show, during the contacting procedure, the pivot levers 21, 22, 23, which are embodied in this way and are pivotably supported in the pivot bearings 531, 532, 533 and coupled to the contact supports 12, 13, 14, move the two contacts 11, 11', which are to be contacted, toward each other in a guided fashion. The paths traveled by the contacts 11, 11 on both sides and thus also their movement times are correspondingly shortened. The selected lever ratios of the pivot levers 21, 22, 23 are advantageously selected so that the two contacts 11, 11' to be contacted each travel half the distance to make the contact via the movement path between the contacts, which by comparison with the movement of only one contact support, significantly reduces the time until the contact is made, such as a reduction on the order of magnitude of 5 ms. This also yields an improvement in the contact making by shortening the bounce times between the contacts, which also contributes to the coupling of the pivot levers 21, 22, 23 to the contact supports 12, 13, 14 in the vicinity of or near the contact regions.

The pivot levers 21, 22, 23 are, for example, stamped out of a flat material and supported with round openings on the pivot bearings 531, 532, 533, which are embodied in the form of protrusions. To permit the pivotable coupling to one another, on the sides of the first and third pivot levers that are oriented toward one another, rounded, arc-shaped coupling sections 212, 232 are cut out, which are engaged in puzzle-like fashion by complementary coupling sections 232, 224 on the middle, second pivot lever 222. In order to immobilize them to prevent a relative movement in relation to each other in the surface direction, the rounded cutouts advantageously embrace the matched, rounded coupling counterpart sections 232, 224 by more than 180°, thus making it easy to insert them into each other in the direction perpendicular to the bearing plate 52. The pivot lever support pieces 211, 221, 222, 231, which protrude at right angles on the flat pivot levers 21, 22, 23, can, for example, be manufactured by right-angled bends of the pivot levers themselves or by bearing pieces affixed to them, possibly with rotary sleeves mounted onto them or produced with low-friction sliding surfaces. With a likewise rounded end section, the armature 30 engages via the free end of the control lever 302 in a matched, rounded recess in the lower lever section of the third pivot lever 23 so that this likewise produces a largely frictionless slide bearing similar to the one between the coupling sections 212, 232 and the coupling counterpart sections 232, 224.

The invention claimed is:

1. A relay for a defibrillator, having a support base (50) on which are mounted a coil (40) and a contacting unit (10) with a contacting mechanism, the contacting unit (10) through excitation of the coil (40) actuatable via an armature (30) and at least one other mechanical intermediate element and having contacts (11, 11') positioned on separate contact supports (12, 13, 14) and can be brought into electrically conductive connection with or separated from each other through activation of the coil (40), the relay comprising: at least one intermediate element formed as a pivot lever coupled to the armature (30) and pivotably coupled to one of the contact supports which supports one of the contacts brought into contact with each other, and an other contact support supporting the other of the contacts (11) to be brought into contact with each other, coupled to an other pivot lever or pivotably coupled directly to the armature (30), and during a contacting procedure, the one and the other contact supports (13, 14) with the contacts (11, 11'), brought into contact with each other, and moved toward each other.

2. A relay for a defibrillator, having a support base (50) on which are mounted a coil (40) and a contacting unlit (10) with a changeover contact mechanism, the contacting unit through electrical excitation of the coil (40) actuatable via an armature (30) and other mechanical intermediate elements and the changeover contact mechanism having at least two lateral contacts (11) supported on lateral contact supports (12, 14) and at least one contact pair (11'), situated between them, is supported on a separate other contact support (13), having contacts on both sides, and, through excitation of the coil (40), can be brought into an electrically conductive connection with the lateral contacts (11) or separated from them in alternating fashion, the relay comprising: the intermediate elements having a pivot lever mechanism coupled to the armature (30), having at least two pivot levers (21, 22, 23), one of which is pivotably coupled to the contact support (13) of the contact pair (11') and at least one of which is pivotably coupled to a lateral contact support (12, 14) separate therefrom, and the pivot levers (21, 22, 23) supported on the support base (50) in pivoting fashion so that both the contact support (13) of the contact pair (11') and the contact support (12, 14) with the lateral contact (11) to be contacted are moved toward each other during a contacting procedure.

3. The relay according to claim 2, wherein at least one of the contact supports (12, 13, 14) is spring-elastic in the pivoting direction.

4. The relay according to claim 3, wherein each of the levers (21, 22, 23) is pivotably supported on a respective fixed hearing element (53), mounted on a bearing plate (52) of the support base (50).

5. The relay according to claim 4, wherein the pivot levers (21, 22, 23) are produced in a form of shaped parts stamped out of a flat material.

6. The relay according to claim 5, wherein the pivot levers (21, 22, 23) are coupled to each other in a pivotable, pivoting-motion-transmitting fashion by coupling sections (212, 232) formed as rounded cut-outs and complementary coupling counterpart sections (223, 224).

7. The relay according to claim 6, wherein between bearing points on a respective bearing element (53) and the respective contact (11, 11'), the pivot levers (21, 22, 23) have at least one pivot lever support piece (211, 221, 222, 231) on which the contact supports (12, 13, 14) of the relevant contacts (11, 11') are supported for a pivoting action.

8. The relay according to claim 7, wherein the relay is used in the defibrillator.

9. The relay according to claim 1, wherein at least one of the contact supports (12, 13, 14) is spring-elastic in the pivoting direction.

10. The relay according to claim 1, wherein each of the levers (21, 22, 23) is pivotably supported on a respective fixed bearing element (53), mounted on a bearing plate (52) of the support base (50).

11. The relay according to claim 1, wherein the pivot levers are produced in a form of shaped parts stamped out of a flat material.

12. The relay according to claim 11, wherein the pivot levers (21, 22, 23) are coupled to each other in a pivotable, pivoting-motion-transmitting fashion by coupling sections (212, 232) formed as rounded cut-outs and complementary coupling counterpart sections (223, 224).

13. The relay according to claim 4, wherein between bearing points on a respective bearing element (53) and the respective contact (11, 11'), the pivot levers (21, 22, 23) have at least one pivot lever support piece (211, 221, 222, 231) on which the contact supports (12, 13, 14) of the relevant contacts (11, 11') are supported for a pivoting action.

14. The relay according to claim 1, wherein the relay is used in the defibrillator.

\* \* \* \* \*